United States Patent [19]

Wiencek

[11] Patent Number: 4,674,494

[45] Date of Patent: Jun. 23, 1987

[54] HUMIDIFYING DEVICE

[75] Inventor: Virginia Wiencek, Claremont, Calif.

[73] Assignee: The Kendall Company, Boston, Mass.

[21] Appl. No.: 732,680

[22] Filed: May 10, 1985

[51] Int. Cl.[4] .......................................... A61M 16/00
[52] U.S. Cl. ......................... 128/203.16; 128/204.13; 261/DIG. 65; 261/104
[58] Field of Search .................... 128/203.16, 203.17, 128/203.27, 203.26, 204.13; 261/DIG. 65, 104, 112, 107

[56] References Cited

U.S. PATENT DOCUMENTS

| | | | |
|---|---|---|---|
| 576,041 | 1/1897 | Denison | 128/204.13 |
| 605,436 | 6/1898 | Kellogg | 128/204.13 |
| 2,083,905 | 6/1937 | Grab | 261/104 |
| 3,285,587 | 11/1966 | Huber | 261/112 |
| 3,432,357 | 3/1969 | Dankese | 261/104 |
| 3,540,445 | 11/1970 | Moyat | 128/204.13 |
| 3,565,071 | 2/1971 | Cobb et al. | 128/204.13 |
| 3,659,604 | 5/1972 | Melville et al. | 128/203.27 |
| 3,954,920 | 5/1976 | Heath | 128/204.13 |
| 4,110,419 | 8/1978 | Miller | 128/203.27 |

Primary Examiner—Henry J. Recla
Attorney, Agent, or Firm—Powell L. Sprunger

[57] ABSTRACT

A humidifying device comprising, an annular cylinder, and a heating device for heating an outer surface of the cylinder. The humidifying device has an annular absorptive column disposed against an inner surface of the cylinder, with the column having a plurality of apertures extending therethrough. The humidifying device has a reservoir containing a sterile liquid, and a conduit connecting the reservoir with the cylinder.

11 Claims, 2 Drawing Figures

HUMIDIFYING DEVICE

BACKGROUND OF THE INVENTION

The present invention relates to humidifying devices.

Humidifying devices of the type for humifyfying and heating a breathable gas such as oxygen supplemented air to be inhaled by a patient undergoing inhalation therapy are known. Such devices may comprise an annular metallic cylinder and a sleeve for heating an outer surface of the cylinder. Such devices also have an annular absorptive column located against an inner surface of the cylinder. Such devices may also have a reservoir containing sterile water, and a conduit connecting a lower portion of the reservoir with a lower portion of the cylinder for flow of water from the reservoir into a lower portion of the cylinder.

Although such devices have operated satisfactorily, difficulty has been found with the absorptive column particularly when the devices have been operated over extended periods of time. It has been found that after operation of a few hours the prior column becomes soft and loses its shape resulting in poor heat conduction from the sleeve. Also, it has been found that pockets of air form between the column and cylinder, which also causes poor heat transfer.

SUMMARY OF THE INVENTION

A principal feature of the present invention is the provision of an improved humidifying device.

The humidifying device of the present invention comprises, an annular cylinder, and means for heating an outer surface of the cylinder. The device has an annular absorptive column disposed against an inner surface of the cylinder. The device also has a reservoir containing a sterile liquid, and conduit means connecting the reservoir with the cylinder.

A feature of the present invention is the provision of apertures extending through the absorptive column.

Another feature of the invention is that the apertures permit the passage of otherwise trapped air through the column.

Thus, a feature of the present invention is that the apertures enhance the heat transfer through the column.

Yet another feature of the invention is that the column comprises a sheet having more than one layer, with aligned apertures to enhance the heat transfer through the column.

A further feature of the invention is that the layers are secured together adjacent one end of the sheet by suitable means, such as by staples.

A feature of the invention is that the secured layers prevent the sheet from losing memory and will thus maintain the absorptive material against the cylinder in order to obtain better heat transfer.

Another feature of the invention is that the secured sheet prevents deformation of the sheet in order to prevent loss of heat transfer.

Further features will become more fully apparent in the following description of the embodiments of this invention and from the appended claims.

DESCRIPTION OF THE PREFERRED EMBODIMENTS

Figure 1:
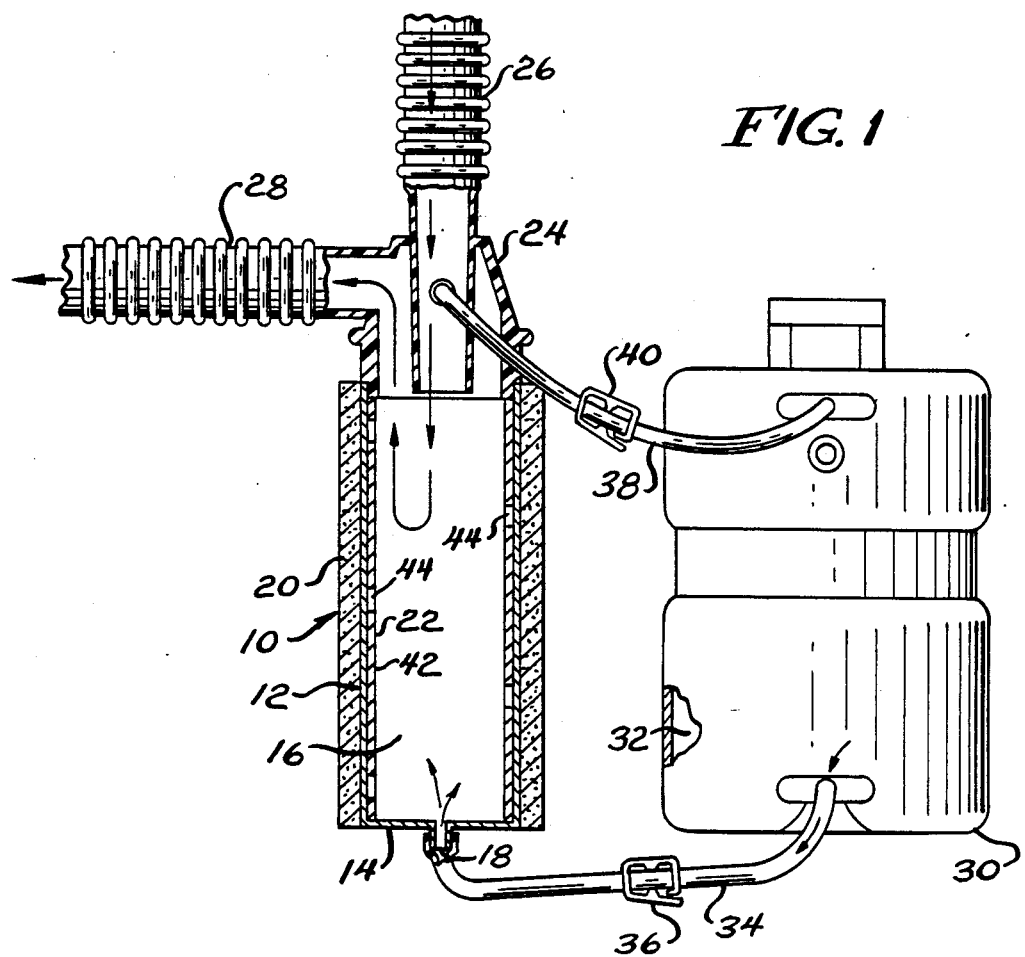
FIG. 1 is a fragmentary elevational view, taken partly in section, of a humidifying device of the present invention.

Referring now to FIG. 1, there is shown a humidifying device generally designated 10 for humidifying and heating a breathable gas to be inhaled by a patient undergoing inhalation therapy. The device 10 has an annular metallic cylinder 12 having a lower wall 14 defining a cavity 16 in the cylinder 12. As shown, the lower wall 14 has a nipple 18 for a purpose which will be described below.

The device 10 has a heating sleeve 20 surrounding the cylinder 12 and placed against an outer surface of the cylinder 12. The sleeve 20 is of known type to the art, and supplies heat through the cylinder 12.

The device 10 has an absorptive column 22 disposed against an inner surface of the cylinder 12. In one form, the column 22 may extend the length of the cylinder 12, as shown. The column 22 draws humidifying liquid into an upper portion of the cylinder 12 for evaporating moisture into the gas directed into the cylinder 12 as will be described below. The column 22 may be constructed of any suitable absorptive material, such as chromatography paper.

The device 10 has a hollow cap 24 secured to an upper portion of the cylinder 12. The cap 24 has a first conduit 26 for passage of a dry oxygen/air mixture from a ventilator or flow meter into the cavity 16 of the cylinder 12, after which the gas mixture is humidified and heated in the cavity 16. The cap 24 has a second conduit 28 for passage of the heated and humidified gas to the patient for inhalation therapy.

The device 10 has a reservoir 30 defining a chamber 32 to retain sterile water for humidifying the gas. The device 10 has a conduit 34 communicating between a lower portion of the reservoir 30 and the nipple 18 of the cylinder 12, such that the sterile water passes through the conduit 34 into a lower portion of the cavity 16 for humidifying the gas. The conduit 34 may have a suitable clamp 36 of known type for selectively closing the conduit 34. The device 10 also has a conduit 38 communicating between an upper portion of the reservoir 30 and the cap 24. The conduit 38 may have a clamp 40 of known type for selectively closing the conduit 38.

In use, the sterile water passes from the reservoir 30 through the conduit 34 into a lower portion of the cavity 16, and some of the water passes upwardly along the absorptive column 22, with heat being supplied by the sleeve 20 to the cylinder 12 and column 22 in order to heat and humidify the gas passing through the first conduit 26, after which the humidified and heated gas passes through the second conduit 28 to the patient.

Figure 2:
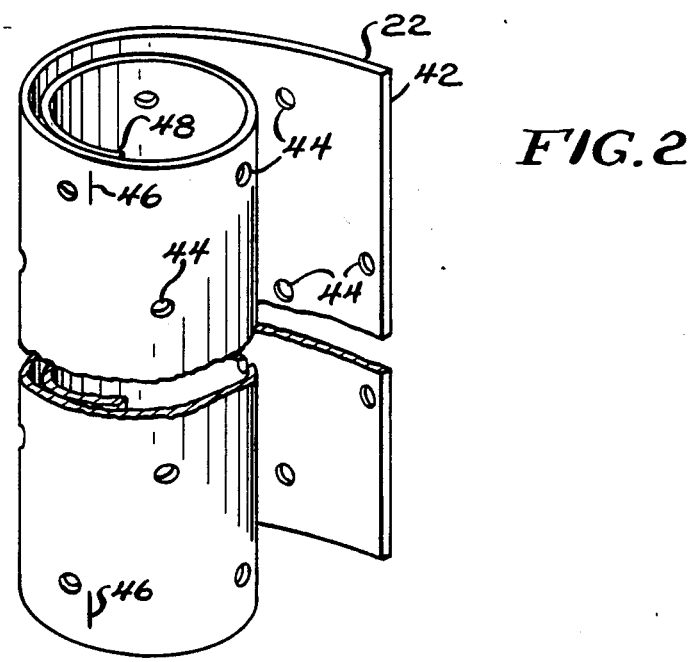
FIG. 2 is a fragmentary perspective view of an absorptive column for the device of FIG. 1.

With reference to FIGS. 1 and 2, the absorptive column 22 of the present invention comprises an elongated sheet 42 of absorptive material. In a preferred form, the sheet 42 has approximately two layers. Also the sheet 42 has a plurality of apertures 44 extending through the sheet 42, with the apertures 44 being aligned in the multiple layers. The layers of the sheet 42 are secured together to prevent spiralling by suitable means, such as by staples 46, at a location adjacent one end 48 of the sheet 42. Other fastening means may be utilized instead of the staples such as follows:(1) other rigid fasteners such as clips or rivets, (2) adhesives, or (3) a slotted tab to lock paper in place.

In use, the layers of the sheet 42 are formed closely together, and the wound sheet 42 is inserted into the cylinder 12, such that the sheet 42 engages against an inner surface of the cylinder 12. During humidification of the device 10, the apertures 44 of the sheet 42 permit captured water vapor to pass through the sheet 42, and thus prevent the sheet 42 from pulling away from the cylinder 12 which would otherwise impair the transfer of heat therethrough. Also, the staples 46 prevent the sheet 42 from losing memory, and will thus maintain the sheet 42 against the cylinder 12 in order to prevent the loss of heat transfer through the sheet 42 to the cavity 16.

The foregoing detailed description is given for clearness of understanding only, and no unnecessary limitations should be understood therefrom, as modifications will be obvious to those skilled in the art.

I claim:

1. A humidifying device for humidifying and heating a breathable gas such as oxygen supplemented air to be inhaled by a patient undergoing inhalation therapy, comprising:

an annular cylinder having walls defining a cavity to retain a liquid;

means for heating an outer surface of said cylinder;

an annular smooth liquid absorptive column disposed in contact against an inner surface of the cylinder peripherally around the cylinder, said column having a plurality of apertures extending therethrough, said column comprising a sheet of absorbent material, and said sheet includes more than one layer, and in which said apertures are aligned through said plural layers;

a reservoir containing sterile liquid;

conduit means connecting the reservoir with the cylinder;

an inlet for connection to a source of breathable gas, said inlet being in fluid communication with the cavity; and an outlet for heated and humidified gas and for connection to gas delivery means to a patient, said outlet being in fluid communication with the cavity.

2. The device of claim 1 wherein the cylinder is constructed from metal.

3. The device of claim 1 wherein the heating means comprises a sleeve surrounding the cylinder.

4. The device of claim 1 wherein said column comprises chromatography paper.

5. The device of claim 1 including means for securing said layers together adjacent one end of the sheet.

6. The device of claim 5 wherein the securing means comprises a plurality of spaced staples.

7. The device of claim 1 including means for securing first and second layers of the sheet together adjacent one end of the sheet.

8. The device of claim 7 wherein the securing means comprises a plurality of staples.

9. The device of claim 1 wherein said sheet has approximately two layers.

10. The device of claim 1 wherein the conduit means connects a lower portion of the reservoir with a lower portion of the cylinder.

11. A humidifying device for humidifying and heating a breathable gas such as oxygen supplemented air to be inhaled by a patient undergoing inhalation therapy, comprising:

an annular cylinder having walls defining a cavity to retain liquid;

means for heating an outer surface of the cylinder;

an annular smooth liquid absorptive column comprising chromatography paper disposed in contact against an inner surface of the cylinder peripherally around the cylinder, said column having a plurality of apertures extending therethrough;

a reservoir containing sterile liquid;

conduit means connecting the reservoir with the cylinder;

an inlet for connection to a source of breathable gas, said inlet being in fluid communication with the cavity; and an outlet for heated and humidified gas and for connection to gas delivery means to a patient, said outlet being in fluid communication with the cavity.

* * * * *